United States Patent
Petermann et al.

(10) Patent No.: US 10,759,874 B2
(45) Date of Patent: *Sep. 1, 2020

(54) GELLING ESTERIFIED CELLULOSE ETHERS

(71) Applicant: Dow Global Technologies LLC, Midland, MI (US)

(72) Inventors: Oliver Petermann, Hamburg (DE); Matthias Knarr, Nienburg/Weser (DE)

(73) Assignee: Dow Global Technologies LLC, Collegeville, Palmyra Atoll ( * ) Notice: Subject to any disclaimer, the term of this patent is extended or adjusted under 35 U.S.C. 154(b) by 14 days.

This patent is subject to a terminal disclaimer.

(21) Appl. No.: 15/550,109

(22) PCT Filed: Mar. 8, 2016

(86) PCT No.: PCT/US2016/021326
§ 371 (c)(1),
(2) Date: Dec. 11, 2017

(87) PCT Pub. No.: WO2016/148976
PCT Pub. Date: Sep. 22, 2016

(65) Prior Publication Data
US 2018/0072820 A1    Mar. 15, 2018

Related U.S. Application Data

(60) Provisional application No. 62/133,518, filed on Mar. 16, 2015.

(51) Int. Cl.
| | |
|---|---|
| C08B 13/00 | (2006.01) |
| C08B 11/20 | (2006.01) |
| A61K 9/14 | (2006.01) |
| A23P 10/30 | (2016.01) |
| A23L 33/125 | (2016.01) |
| A61K 9/10 | (2006.01) |
| A61K 9/48 | (2006.01) |
| A61K 47/38 | (2006.01) |

(52) U.S. Cl.
CPC ............ *C08B 13/00* (2013.01); *A23L 33/125* (2016.08); *A23P 10/30* (2016.08); *A61K 9/10* (2013.01); *A61K 9/146* (2013.01); *A61K 9/4816* (2013.01); *A61K 47/38* (2013.01); *C08B 11/20* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,226,981 | A | 10/1980 | Onda et al. |
| 4,365,060 | A | 12/1982 | Onda et al. |
| 5,776,501 | A | 7/1998 | Kokubo et al. |
| 2012/0161364 | A1 | 6/2012 | Son et al. |

FOREIGN PATENT DOCUMENTS

| | | |
|---|---|---|
| EP | 0219426 | 4/1987 |
| EP | 2476439 A1 | 7/2012 |
| JP | 2013-504565 A | 2/2013 |
| JP | 6356922 B2 | 7/2018 |
| JP | 6371482 B2 | 8/2018 |
| WO | 2005115330 | 12/2005 |
| WO | 2011159626 A1 | 12/2011 |
| WO | 2013148154 A1 | 10/2013 |
| WO | 2013154607 A1 | 10/2013 |
| WO | 2013164121 A1 | 11/2013 |
| WO | 2014031419 A1 | 2/2014 |
| WO | 2014031422 A1 | 2/2014 |
| WO | 2014031447 A1 | 2/2014 |
| WO | 2014137777 A1 | 9/2014 |
| WO | 2014137778 A1 | 9/2014 |
| WO | 2014137779 A1 | 9/2014 |
| WO | WO-2016/148970 A1 | 9/2016 |
| WO | WO-2016/148977 A1 | 9/2016 |

OTHER PUBLICATIONS

Zhang, L.-L. et al., Synthesis of Hydroxypropyl Methylcellulose Acetate Succinate. Fine Chem. 2012; 29(10):980-4 (English Abstract Included).
McGinity, Aqueous Polymeric Coatings for Pharmaceutical Dosage Forms, The University of Texas at Austin, 1989.
Rowe et al., Handbook of Pharmaceutical Excipients, 6th edition, Pharmaceutical Press, 2010.
Aqoat, Shin-Etsu Chemical Co. Ltd.

*Primary Examiner* — Jessica Worsham

(57) ABSTRACT

An esterified cellulose comprising aliphatic monovalent acyl groups and groups of the formula —C(O)—R—COOH, R being a divalent hydrocarbon group, has the following properties: i) the degree of neutralization of the groups —C(O)—R—COOH is not more than 0.4, ii) the total degree of ester substitution is from 0.03 to 0.38, and iii) the esterified cellulose ether has a solubility in water of at least 2.0 weight percent at 20° C.

17 Claims, 2 Drawing Sheets

GELLING ESTERIFIED CELLULOSE ETHERS

This application represents a national filing under 35 U.S.C. 371 of International Application No. PCT/US2016/021326 filed Mar. 8, 2016, and claims priority of U.S. Provisional Application No. 62/133,518 filed Mar. 16, 2015.

FIELD

This invention concerns novel esterified cellulose ethers and their use for producing capsule shells or for coating dosage forms.

INTRODUCTION

Esters of cellulose ethers, their uses and processes for preparing them are generally known in the art, for examples for improving the water solubility of poorly water-soluble drugs or for preparing capsules or coatings.

A large number of presently known drugs have a low solubility in water, and thus complex techniques are required to prepare a dosage form. One known method includes dissolving such drug together with a pharmaceutically acceptable water-soluble polymer, such as hydroxypropyl methyl cellulose acetate succinate (HPMCAS), in a blend of organic solvent and water and to spray-dry the solution. The pharmaceutically acceptable water-soluble polymer is aimed at reducing the crystallinity of the drug, thereby minimizing the activation energy necessary for the dissolution of the drug, as well as establishing hydrophilic conditions around the drug molecules, thereby improving the solubility of the drug itself to increase its bioavailability, i.e., its in vivo absorption by an individual upon ingestion.

International Patent Application WO 2005/115330 discloses HPMCAS polymers with a specific combination of degrees of substitution. The HPMCAS polymer has a degree of substitution of succinoyl groups ($DOS_S$) of at least 0.02, a degree of substitution of acetyl groups ($DOS_{Ac}$) of at least 0.65 and a sum of $DOS_{Ac}$ and $DOS_S$ of at least 0.85. WO 2005/115330 discloses that the increased acetate substitution allows increased solubility of active agents in spray-dried solutions, while the increased succinate substitution increases the solubility of the polymer in aqueous solution.

International Patent Application WO 2011/159626 discloses an active ingredient and HPMCAS having a degree of substitution of methoxy groups ($DS_M$) of ≤1.45, and a combined degree of substitution of acetyl groups ($DS_{Ac}$) and succinoyl groups ($DS_s$) of ($DS_{Ac}+DS_s$)≥1.25.

When the esterified cellulose ethers comprise ester groups which carry carboxylic groups, the solubility of the esterified cellulose ethers in aqueous liquids is typically dependent on the pH. For example, the solubility of hydroxypropyl methyl cellulose acetate succinate (HPMCAS) in aqueous liquids is pH-dependent due to the presence of succinate groups, also called succinyl groups or succinoyl groups. The pH-dependent solubility is dependent on the degree of substitution of acidic functional groups. The dissolution time of various types of HPMCAS dependent on pH and on the degree of neutralization of HPMCAS is discussed in detail in McGinity, James W. *Aqueous Polymeric Coatings for Pharmaceutical Dosage Forms*, New York: M. Dekker, 1989, pages 105-113. The above-mentioned article *Aqueous Polymeric Coatings for Pharmaceutical Dosage Forms* illustrates in FIG. 16 on p. 112 the dissolution time of several grades of HPMCAS, which have different degrees of substitution with succinoyl, acetyl and methoxyl groups, in pure water and in 0.1 N NaCl depending on the degree of neutralization of the HPMCAS. Depending on the HPMCAS and the presence or absence of NaCl, HPMCAS is soluble when it has a degree of neutralization between about 0.55 and 1. Below a degree of neutralization of about 0.55, all HPMCAS grades are insoluble in pure water and in 0.1 N NaCl.

International Patent Application WO 2013/164121 teaches that many techniques for preparing capsules from HPMCAS still require salts or pH regulators leading to water sensitivity or brittleness of the resulting capsule shells, require multiple processing steps, and/or need to be processed in non-aqueous media. To solve these problems, WO 2013/164121 discloses an aqueous composition comprising HPMCAS polymer dispersed in water, wherein the polymer is partially neutralized with at least one alkaline material, such as ammonia, sodium hydroxide, calcium hydroxide, potassium hydroxide, cationic polymers, and mixtures thereof.

There is still the urgent need to provide novel esterified cellulose ethers which are useful for improving the water solubility of poorly water-soluble drugs, for preparing capsules or for coating dosage forms which do not require the presence of a pH regulator to be soluble in water. Particularly, it would be desirable to provide novel esterified cellulose ethers which carry carboxylic groups and which are soluble in water even when the majority of the carboxylic groups are not neutralized.

Surprisingly, novel esterified cellulose ethers carrying carboxylic groups have been found which are soluble in water although the degree of neutralization of the carboxylic groups is not more than 0.4. Even more surprisingly, it has been found that aqueous solutions of these novel esterified cellulose ethers can be prepared at room temperature and that the aqueous solutions gel at elevated temperature, which makes them very suitable for coating dosage forms or for producing capsule shells.

SUMMARY

One aspect of the present invention is an esterified cellulose ether which comprises aliphatic monovalent acyl groups and groups of the formula —C(O)—R—COOH, R being a divalent hydrocarbon group, wherein i) the degree of neutralization of the groups —C(O)—R—COOH is not more than 0.4, ii) the total degree of ester substitution is from 0.03 to 0.38, and iii) the esterified cellulose ether has a solubility in water of at least 2.0 weight percent at 20° C.

Another aspect of the present invention is an aqueous composition which comprises an above-described esterified cellulose ether dissolved in an aqueous diluent.

Yet another aspect of the present invention is a liquid composition which comprises at an above-described esterified cellulose ether and an organic diluent.

Yet another aspect of the present invention is a process for coating a dosage form which comprises the step of contacting an above-mentioned composition with the dosage form.

Yet another aspect of the present invention is a process for the manufacture of capsule shells which comprises the step of contacting an above-mentioned composition with dipping pins.

Yet another aspect of the present invention is a coated dosage form wherein the coating comprises at least one above-described esterified cellulose ether.

Yet another aspect of the present invention is a polymeric capsule shell which comprises at least one above-described esterified cellulose ether.

Yet another aspect of the present invention is a capsule which comprises the above-mentioned capsule shell and further comprises a drug or a nutritional or food supplement or a combination thereof.

Yet another aspect of the present invention is a solid dispersion of at least one active ingredient in at least one above-described esterified cellulose ether.

DESCRIPTION OF EMBODIMENTS

Figure 1A:
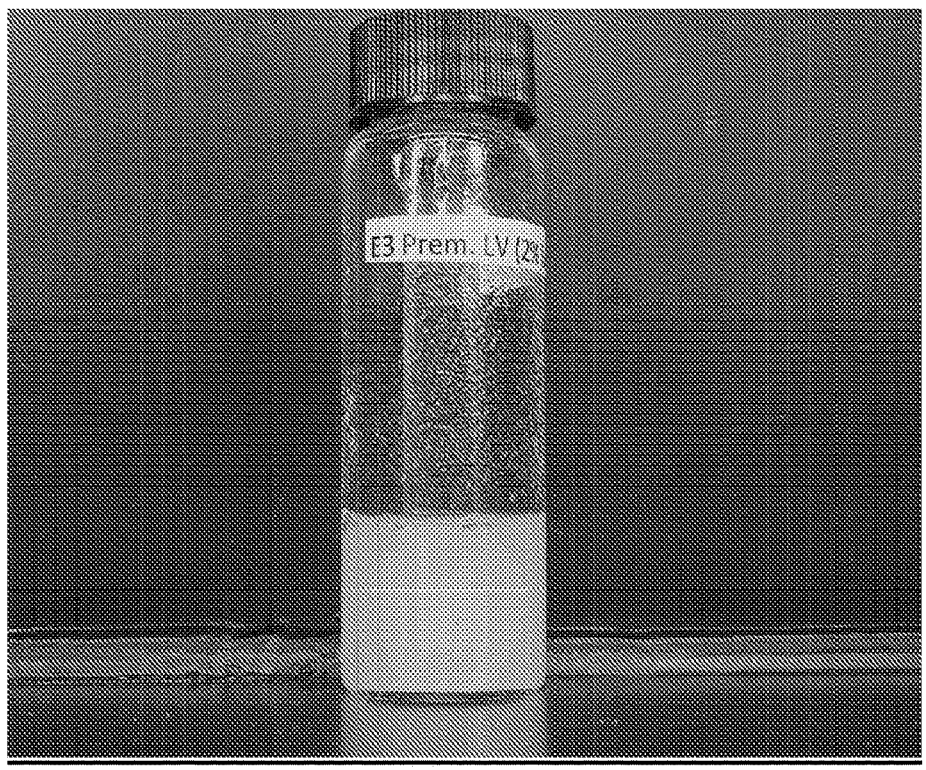
FIG. 1A is a photographical representation of a 2 wt.-% solution of hydroxypropyl methyl cellulose (HPMC) in water used as starting material for preparing HPMCAS after heating to 70° C.

Surprisingly, it has been found that the esterified cellulose ethers of the present invention have a solubility in water of at least 2.0 weight percent at 20° C. Clear or turbid solutions without sediment are obtained at 20° C. Moreover, aqueous solutions of the esterified cellulose ether of the present invention gel at elevated temperature. This renders the esterified cellulose ether of the present invention very useful in a variety of application, e.g. for producing capsules or for coating dosage forms. The advantages of the esterified cellulose ether of the present invention will be described in more detail below.

The esterified cellulose ether has a cellulose backbone having β-1,4 glycosidically bound D-glucopyranose repeating units, designated as anhydroglucose units in the context of this invention. The esterified cellulose ether preferably is an esterified alkyl cellulose, hydroxyalkyl cellulose or hydroxyalkyl alkylcellulose. This means that in the esterified cellulose ether of the present invention, at least a part of the hydroxyl groups of the anhydroglucose units are substituted by alkoxyl groups or hydroxyalkoxyl groups or a combination of alkoxyl and hydroxyalkoxyl groups. The hydroxyalkoxyl groups are typically hydroxymethoxyl, hydroxyethoxyl and/or hydroxypropoxyl groups. Hydroxyethoxyl and/or hydroxypropoxyl groups are preferred. Typically one or two kinds of hydroxyalkoxyl groups are present in the esterified cellulose ether. Preferably a single kind of hydroxyalkoxyl group, more preferably hydroxypropoxyl, is present. The alkoxyl groups are typically methoxyl, ethoxyl and/or propoxyl groups. Methoxyl groups are preferred. Illustrative of the above-defined esterified cellulose ethers are esterified alkylcelluloses, such as esterified methylcelluloses, ethylcelluloses, and propylcelluloses; esterified hydroxyalkylcelluloses, such as esterified hydroxyethylcelluloses, hydroxypropylcelluloses, and hydroxybutylcelluloses; and esterified hydroxyalkyl alkylcelluloses, such as esterified hydroxyethyl methylcelluloses, hydroxymethyl ethylcelluloses, ethyl hydroxyethylcelluloses, hydroxypropyl methylcelluloses, hydroxypropyl ethylcelluloses, hydroxybutyl methylcelluloses, and hydroxybutyl ethylcelluloses; and those having two or more hydroxyalkyl groups, such as esterified hydroxyethylhydroxypropyl methylcelluloses. Most preferably, the esterified cellulose ether is an esterified hydroxyalkyl methylcellulose, such as an esterified hydroxypropyl methylcellulose.

The degree of the substitution of hydroxyl groups of the anhydroglucose units by hydroxyalkoxyl groups is expressed by the molar substitution of hydroxyalkoxyl groups, the MS(hydroxyalkoxyl). The MS(hydroxyalkoxyl) is the average number of moles of hydroxyalkoxyl groups per anhydroglucose unit in the esterified cellulose ether. It is to be understood that during the hydroxyalkylation reaction the hydroxyl group of a hydroxyalkoxyl group bound to the cellulose backbone can be further etherified by an alkylation agent, e.g. a methylation agent, and/or a hydroxyalkylation agent. Multiple subsequent hydroxyalkylation etherification reactions with respect to the same carbon atom position of an anhydroglucose unit yields a side chain, wherein multiple hydroxyalkoxyl groups are covalently bound to each other by ether bonds, each side chain as a whole forming a hydroxyalkoxyl substituent to the cellulose backbone.

The term "hydroxyalkoxyl groups" thus has to be interpreted in the context of the MS(hydroxyalkoxyl) as referring to the hydroxyalkoxyl groups as the constituting units of hydroxyalkoxyl substituents, which either comprise a single hydroxyalkoxyl group or a side chain as outlined above, wherein two or more hydroxyalkoxy units are covalently bound to each other by ether bonding. Within this definition it is not important whether the terminal hydroxyl group of a hydroxyalkoxyl substituent is further alkylated, e.g. methylated, or not; both alkylated and non-alkylated hydroxyalkoxyl substituents are included for the determination of MS(hydroxyalkoxyl). The esterified cellulose ether of the invention generally has a molar substitution of hydroxyalkoxyl groups in the range 0.05 to 1.00, preferably 0.08 to 0.70, more preferably 0.15 to 0.60, most preferably 0.15 to 0.40, and particularly 0.20 to 0.40.

The average number of hydroxyl groups substituted by alkoxyl groups, such as methoxyl groups, per anhydroglucose unit, is designated as the degree of substitution of alkoxyl groups, DS(alkoxyl). In the above-given definition of DS, the term "hydroxyl groups substituted by alkoxyl groups" is to be construed within the present invention to include not only alkylated hydroxyl groups directly bound to the carbon atoms of the cellulose backbone, but also alkylated hydroxyl groups of hydroxyalkoxyl substituents bound to the cellulose backbone. The esterified cellulose ethers according to this invention generally have a DS(alkoxyl) in the range of 1.0 to 2.5, preferably from 1.2 to 2.2, more preferably from 1.6 to 2.05, and most preferably from 1.7 to 2.05.

Most preferably the esterified cellulose ether is an esterified hydroxypropyl methylcellulose having a DS(methoxyl) within the ranges indicated above for DS(alkoxyl) and an MS(hydroxypropoxyl) within the ranges indicated above for MS(hydroxyalkoxyl).

The esterified cellulose ether of the present invention comprises as ester groups the groups of the formula —C(O)—R—COOH, wherein R is a divalent hydrocarbon group, such as —C(O)—CH$_2$—CH$_2$—COOH, and aliphatic monovalent acyl groups, such as acetyl, propionyl, or butyryl, such as n-butyryl or i-butyryl. Specific examples of esterified cellulose ethers are hydroxypropyl methylcellulose acetate succinate (HPMCAS), hydroxypropyl cellulose acetate succinate (HPCAS), hydroxybutyl methyl cellulose propionate succinate (HBMCPrS), hydroxyethyl hydroxypropyl cellulose propionate succinate (HEHPCPrS), or methyl cellulose acetate succinate (MCAS). Hydroxypropyl methylcellulose acetate succinate (HPMCAS) is the most preferred esterified cellulose ether.

An essential feature of the esterified cellulose ethers of the present invention is their total degree of ester substitution, specifically the sum of i) the degree of substitution of aliphatic monovalent acyl groups and ii) the degree of substitution of groups of formula —C(O)—R—COOH. The total degree of ester substitution is at least 0.03, preferably at least 0.05, more preferably at least 0.07, even preferably at least 0.09, and most preferably at least 0.11. The total degree of ester substitution is not more than 0.38, preferably up to 0.35, more preferably up to 0.31, even more preferably up to 0.27, and most preferably up to 0.20. The esterified cellulose ethers form clear solutions in water at a concentration of 2 wt.-% at 20° C.

The esterified cellulose ethers of the present invention generally have a degree of substitution of aliphatic monovalent acyl groups, such as acetyl, propionyl, or butyryl groups, of at least 0.01, preferably at least 0.02, more preferably at least 0.03, and most preferably at least 0.04. The esterified cellulose ethers generally have a degree of substitution of aliphatic monovalent acyl groups of up to 0.35, preferably up to 0.30, more preferably up to 0.25, and most preferably up to 0.20.

The esterified cellulose ethers of the present invention generally have a degree of substitution of groups of formula —C(O)—R—COOH, such as succinoyl, of at least 0.005, preferably at least 0.01, and more preferably at least 0.02. The esterified cellulose ethers generally have a degree of substitution of groups of formula —C(O)—R—COOH of up to 0.18, preferably up to 0.16, and more preferably up to 0.14.

Moreover, the sum of i) the degree of substitution of aliphatic monovalent acyl groups and ii) the degree of substitution of groups of formula —C(O)—R—COOH and iii) the degree of substitution of alkoxyl groups, DS(alkoxyl), generally is not more than 2.40, preferably not more than 2.30, more preferably not more than 2.25, and most preferably not more than 2.20. Esterified cellulose ethers having such sum of degrees of substitution generally form clear solutions in water at a concentration of 2 wt.-%. The esterified cellulose ethers generally have a sum of degrees of substitution of i) aliphatic monovalent acyl groups and ii) groups of formula —C(O)—R—COOH and iii) of alkoxyl groups of at least 1.60, preferably at least 1.75, more preferably at least 1.90, and most preferably at least 2.00.

The content of the acetate and succinate ester groups is determined according to "Hypromellose Acetate Succinate, United States Pharmacopia and National Formulary, NF 29, pp. 1548-1550". Reported values are corrected for volatiles (determined as described in section "loss on drying" in the above HPMCAS monograph). The method may be used in analogue manner to determine the content of propionyl, butyryl and other ester groups.

The content of ether groups in the esterified cellulose ether is determined in the same manner as described for "Hypromellose", United States Pharmacopeia and National Formulary, USP 35, pp 3467-3469.

The contents of ether and ester groups obtained by the above analyses are converted to DS and MS values of individual substituents according to the formulas below. The formulas may be used in analogue manner to determine the DS and MS of substituents of other cellulose ether esters.

$$\% \text{ cellulose backbone} = 100 - \left(\% \text{ MeO} * \frac{M(OCH_3) - M(OH)}{M(OCH_3)}\right) -$$
$$\left(\% \text{ HPO} * \frac{M(OCH_2CH(OH)CH_3) - M(OH)}{M(OCH_2CH(OH)CH_3)}\right) -$$
$$\left(\% \text{ Acetyl} * \frac{M(COCH_3) - M(H)}{M(COCH_3)}\right) -$$
$$\left(\% \text{ Succinoyl} * \frac{M(COC_2H_4COOH) - M(H)}{M(COC_2H_4COOH)}\right)$$

$$DS(\text{Me}) = \frac{\frac{\% \text{ MeO}}{M(OCH_3)}}{\frac{\% \text{ cellulose backbone}}{M(AGU)}} \quad MS(\text{HP}) = \frac{\frac{\% \text{ HPO}}{M(HPO)}}{\frac{\% \text{ cellulose backbone}}{M(AGU)}}$$

$$DS(\text{Acetyl}) = \frac{\frac{\% \text{ Acetyl}}{M(\text{Acetyl})}}{\frac{\% \text{ cellulose backbone}}{M(AGU)}}$$

$$DS(\text{Succinoyl}) = \frac{\frac{\% \text{ Succinoyl}}{M(\text{Succinoyl})}}{\frac{\% \text{ cellulose backbone}}{M(AGU)}}$$

$M(\text{MeO}) = M(OCH_3) = 31.03\ Da$ $M(\text{HPO}) = M(OCH_2CH(OH)CH_3) = 75.09\ Da$ $M(\text{Acetyl}) = M(COCH_3) = 43.04\ Da$ $M(\text{Succinoyl}) = M(COC_2H_4COOH) = 101.08\ Da$ $M(\text{AGU}) = 162.14\ Da \quad M(\text{OH}) = 17.008\ Da \quad M(\text{H}) = 1.008\ Da$ By convention, the weight percent is an average weight percentage based on the total weight of the cellulose repeat unit, including all substituents. The content of the methoxyl group is reported based on the mass of the methoxyl group (i.e., —OCH$_3$). The content of the hydroxyalkoxyl group is reported based on the mass of the hydroxyalkoxyl group (i.e., —O— alkylene-OH); such as hydroxypropoxyl (i.e., —O—CH$_2$CH(CH$_3$)—OH). The content of the aliphatic monovalent acyl groups is reported based on the mass of —C(O)—R$_1$ wherein R$_1$ is a monovalent aliphatic group, such as acetyl (—C(O)—CH$_3$). The content of the group of formula —C(O)—R—COOH is reported based on the mass of this group, such as the mass of succinoyl groups (i.e., —C(O)—CH$_2$—CH$_2$—COOH).

The esterified cellulose ethers of the present invention generally have a weight average molecular weight M$_w$ of up to 500,000 Dalton, preferably up to 200,000 Dalton, more preferably up to 150,000 Dalton, and most preferably up to 100,000 Dalton or up to 50,000 Dalton. Generally they have a weight average molecular weight M$_w$ of at least 10,000 Dalton, preferably at least 15,000 Dalton, more preferably at least 20,000 Dalton, and most preferably at least 25,000 Dalton.

The esterified cellulose ethers of the present invention generally have a Polydispersity M$_w$/M$_n$, i.e., a ratio of weight average molecular weight M$_w$ to number average molecular weight M$_n$, of at least 1.2, typically at least 1.3. Moreover, the esterified cellulose ethers of the present invention generally have a Polydispersity of up to 2.6, preferably of up to 2.3, more preferably of up to 1.9, and most preferably up to 1.6.

M$_w$ and M$_n$ are measured according to Journal of Pharmaceutical and Biomedical Analysis 56 (2011) 743 using a mixture of 40 parts by volume of acetonitrile and 60 parts by volume of aqueous buffer containing 50 mM $NaH_2PO_4$ and 0.1 M $NaNO_3$ as mobile phase. The mobile phase is adjusted to a pH of 8.0. The measurement of $M_w$ and $M_n$ is described in more details in the Examples.

In the esterified cellulose ether of the present invention the degree of neutralization of the groups —C(O)—R—COOH is not more than 0.4, preferably not more than 0.3, more preferably not more than 0.2, most preferably not more than 0.1, and particularly not more than 0.05 or even not more than 0.01. The degree of neutralization can even be essentially zero or only slightly above it, e.g. up to $10^{-3}$ or even only up to $10^{-4}$. The term "degree of neutralization" as used herein defines the ratio of deprotonated carboxylic groups over the sum of deprotonated and protonated carboxylic groups, i.e., Degree of neutralization=[—C(O)—R—COO$^-$]/[—C(O)—R—COO$^-$+—C(O)—R—COOH].

Another essential property of the esterified cellulose ether of the present invention is its water-solubility. Surprisingly, the esterified cellulose ether of the present invention has a solubility in water of at least 2.0 weight percent at 20° C., i.e., it can be dissolved as an at least 2.0 weight percent solution, preferably at least 3.0 weight percent solution, more preferably at least 5.0 weight percent solution, and most preferably even at least 10.0 weight percent solution in water at 20° C. Generally the esterified cellulose ether of the present invention can be dissolved as up to 20 weight percent solution or in the most preferred embodiments even as up to 30 weight percent solution in water at a temperature of 20° C. The term "an x weight percent solution in water at 20° C." as used herein means that x g of the esterified cellulose ether is soluble in (100–x) g of water at 20° C.

When determining the water solubility as described in the Examples section, the esterified cellulose ether of the present invention preferably has solubility properties that at least 85 wt. %, typically at least 90 wt. %, more typically at least 95 wt. %, and in most cases at least 99 wt. % of the esterified cellulose ether is soluble in a mixture of 2.5 weight parts of the esterified cellulose ether and 97.5 weight parts of water at 2° C. Typically this degree of solubility is also observed in a mixture of 5 or 10 weight parts of the esterified cellulose ether and 95 or 90 weight parts of water at 2° C. or even in a mixture of 20 weight parts of the esterified cellulose ether and 80 weight parts of water at 2° C.

In more general terms, it has surprisingly been found that the esterified cellulose ether of the present invention, in spite of its low degree of neutralization of the groups —C(O)—R—COOH, is soluble in an aqueous liquid at a temperature of 20° C., even when the esterified cellulose ether is blended with an aqueous liquid that does not increase the degree of neutralization of the esterified cellulose ether to more than 0.4 or a preferred range listed above, e.g., when the esterified cellulose ether is blended with only water, such as deionized or distilled water. Clear or turbid solutions without sediment are obtained at 20° C. Moreover, it has been found that aqueous solutions of an esterified cellulose ether of the present invention gel at elevated temperature, typically at 50 to 90° C., more typically at 60 to 80° C. This renders the esterified cellulose ether of the present invention very useful in a variety of application, e.g. for producing capsules and for coating dosage forms. Very surprisingly, esterified cellulose ethers are provided by the present invention which gel at elevated temperature when they are dissolved in water. Even more surprisingly, gelling of aqueous solutions of the esterified cellulose ethers, such as hydroxypropyl methyl cellulose acetate succinates (HPMCAS), at elevated temperature is observed even when aqueous solutions of the cellulose ethers that are used as starting materials for producing the esterified cellulose ethers do not gel. E.g., the Examples of the present invention illustrate gelling HPMCAS of the present invention, although the corresponding hydroxypropyl methyl cellulose that is used as a starting material for preparing them does not gel to a significant degree. Gelation of the esterified cellulose ethers of the present invention even occurs at low concentration, such as 0.5 to 30 weight percent, typically at 1 to 25 weight percent, and more typically at 2 to 20 weight percent, based on the total weight of esterified hydroxyalkyl alkyl cellulose and aqueous liquid. The esterified cellulose ether of the present invention, specifically the HPMCAS materials, even are transformed into firm, elastic gels at an elevated temperature as described above. The gelation is reversible, i.e. upon cooling to 20° C. the gel transforms into a liquid aqueous solution.

The aqueous liquid in which the esterified cellulose ether of the present invention is soluble may additionally comprise a minor amount of an organic liquid diluent; however, the aqueous liquid should generally comprise at least 80, preferably at least 85, more preferably at least at least 90, and particularly at least 95 weight percent of water, based on the total weight of the aqueous liquid. The term "organic liquid diluent" as used herein means an organic solvent or a mixture of two or more organic solvents. Preferred organic liquid diluents are polar organic solvents having one or more heteroatoms, such as oxygen, nitrogen or halogen like chlorine. More preferred organic liquid diluents are alcohols, for example multifunctional alcohols, such as glycerol, or preferably monofunctional alcohols, such as methanol, ethanol, isopropanol or n-propanol; ethers, such as tetrahydrofuran, ketones, such as acetone, methyl ethyl ketone, or methyl isobutyl ketone; acetates, such as ethyl acetate; halogenated hydrocarbons, such as methylene chloride; or nitriles, such as acetonitrile. More preferably the organic liquid diluents have 1 to 6, most preferably 1 to 4 carbon atoms. The aqueous liquid may comprise a basic compound, but the degree of neutralization of the groups —C(O)—R—COOH of the esterified cellulose ether in the resulting blend of esterified cellulose ether and aqueous liquid should not be more than 0.4, preferably not more than 0.3 or 0.2 or 0.1, more preferably not more than 0.05 or 0.01, and most preferably not more than $10^{-3}$ or even not more than $10^{-4}$. Preferably the aqueous liquid does not comprise a substantial amount of a basic compound. More preferably, the aqueous diluent does not contain a basic compound. Even more preferably, the aqueous liquid comprises from 80 to 100 percent, preferably 85 to 100 percent, more preferably 90 to 100 percent and most preferably 95 to 100 percent of water, and from 0 to 20 percent, preferably 0 to 15 percent, more preferably 0 to 10 percent, and most preferably 0 to 5 percent of an organic liquid diluent, based on the total weight of the aqueous liquid. Most preferably the aqueous liquid consists of water, e.g., deionized or distilled water.

The esterified cellulose ethers of the present invention generally have a viscosity of up to 200 mPa·s, preferably up to 100 mPa·s, more preferably up to 50 mPa·s, and most preferably up to 5.0 mPa·s, measured as a 2.0 wt.-% solution of the esterified cellulose ether in 0.43 wt.-% aqueous NaOH at 20° C. Generally the viscosity is at least 1.2 mPa·s, more typically at least 1.8 mPa·s, even more typically at least 2.4 mPa·s, and most typically at least 2.8 mPa·s, measured as a 2.0 wt.-% solution of the esterified cellulose ether in 0.43 wt.-% aqueous NaOH at 20° C. The 2.0% by weight solution of the esterified cellulose ether is prepared as described in "Hypromellose Acetate Succinate, United States Pharmacopeia and National Formulary, NF 29, pp. 1548-1550", followed by an Ubbelohde viscosity measurement according to DIN 51562-1:1999-01 (January 1999).

Details of the production of the esterified cellulose ethers of the present invention are described in the examples. Some aspects of the production process are described below. The esterified cellulose ether of the present invention can be produced by esterifying a cellulose ether, such as an alkyl cellulose, hydroxyalkyl cellulose or hydroxyalkyl alkylcellulose described further above. The cellulose ethers preferably have a DS(alkoxyl) and/or an MS(hydroxyalkoxyl) as described further above. The cellulose ether used as a starting material in the process of the present invention generally has a viscosity of from 1.2 to 200 mPa·s, preferably from 1.8 to 100 mPa·s, more preferably from 2.4 to 50 mPa·s and in particular from 2.8 to 5.0 mPa·s, measured as a 2 weight-% aqueous solution at 20° C. according to ASTM D2363-79 (Reapproved 2006). Cellulose ethers of such viscosity can be obtained by subjecting a cellulose ether of higher viscosity to a partial depolymerization process. Partial depolymerization processes are well known in the art and described, for example, in European Patent Applications EP 1,141,029; EP 210,917; EP 1,423,433; and U.S. Pat. No. 4,316,982. Alternatively, partial depolymerization can be achieved during the production of the cellulose ethers, for example by the presence of oxygen or an oxidizing agent.

The cellulose ether is reacted with an aliphatic monocarboxylic acid anhydride, such as acetic anhydride, butyric anhydride and propionic anhydride, and with a dicarboxylic acid anhydride, such as succinic anhydride. The molar ratio between the anhydride of an aliphatic monocarboxylic acid and the anhydroglucose units of the cellulose ether generally is from 0.05/1 to 0.35, preferably from 0.09 to 0.30. The molar ratio between the anhydride of a dicarboxylic acid and the anhydroglucose units of cellulose ether generally is from 0.01 to 0.30, preferably from 0.02 to 0.26. The ratio between the total molar amounts of these anhydrides and the anhydroglucose units generally is from 0.20/1 to 0.45/1, preferably from 0.24/1 to 0.40/1.

The molar number of anhydroglucose units of the cellulose ether utilized in the process can be determined from the weight of the cellulose ether used as a starting material, by calculating the average molecular weight of the substituted anhydroglucose units from the DS(alkoxyl) and MS(hydroxyalkoxyl).

The esterification of the cellulose ether is conducted in an aliphatic carboxylic acid as a reaction diluent, such as acetic acid, propionic acid, or butyric acid. The reaction diluent can comprise minor amounts of other solvents or diluents which are liquid at room temperature and do not react with the cellulose ether, such as aromatic or aliphatic solvents like benzene, toluene, 1,4-dioxane, or tetrahydrofurane; or halogenated $C_1$-$C_3$ derivatives, like dichloro methane or dichloro methyl ether, but the amount of the aliphatic carboxylic acid should generally be more than 50 percent, preferably at least 75 percent, and more preferably at least 90 percent, based on the total weight of the reaction diluent. Most preferably the reaction diluent consists of an aliphatic carboxylic acid. The molar ratio [aliphatic carboxylic acid/anhydroglucose units of cellulose ether] generally is from 7.0/1 to 9.0/1, preferably from 7.3/1 to 8.8/1.

The esterification reaction is conducted in the presence of an esterification catalyst, preferably in the presence of an alkali metal carboxylate, such as sodium acetate or potassium acetate. The molar ratio [alkali metal carboxylate/anhydroglucose units of cellulose ether] is generally from [2.0/1.0] to [3.0/1.0], and preferably from [2.3/1.0] to [2.6/1.0].

The reaction temperature for the esterification is generally from 75° C. to 95° C., preferably from 80° C. to 90° C. The esterification reaction is typically completed within 2.5 to 4 hours. After completion of the esterification reaction, the esterified cellulose ether can be precipitated from the reaction mixture in a known manner, for example as described in U.S. Pat. No. 4,226,981, International Patent Application WO 2005/115330, European Patent Application EP 0 219 426 or International Patent Application WO2013/148154. The precipitated esterified cellulose ether is typically washed with an aqueous liquid at a temperature of from 70 to 100° C. Suitable aqueous liquids are described further above.

Another aspect of the present invention is an aqueous composition comprising one or more of the above described esterified cellulose ethers of the present invention dissolved in an aqueous liquid. The aqueous liquid is a described further above. The esterified cellulose ether of the present invention can be brought into aqueous solution at room temperature (about 20° C.), which is a great advantage of the esterified cellulose ethers of the present invention. The aqueous composition preferably comprises at least 5 wt.-%, more preferably at least 10 wt.-%, and preferably up to 30 wt.-%, more preferably up to 20 wt.-% of the esterified cellulose ether of the present invention, based on the total weight of the aqueous composition.

The aqueous composition comprising one or more of the above described esterified cellulose ethers of the present invention dissolved in an aqueous liquid is useful in the manufacture of capsules which comprises the step of contacting the liquid composition with dipping pins. The capsules can even be prepared at about room temperature, which results in savings in energy. Typically an aqueous composition having a temperature of less than 23° C., more typically less than 15° C. or in some embodiments less than 10° C. is contacted with dipping pins having a higher temperature than the aqueous composition and that have a temperature of at least 21° C., typically at least 25° C., more typically at least 50° C. and up to 95° C., preferably up to 80° C.

The aqueous composition comprising one or more of the above described esterified cellulose ethers dissolved in an aqueous liquid is also useful for coating dosage forms, such as tablets, granules, pellets, caplets, lozenges, suppositories, pessaries or implantable dosage forms.

Another aspect of the present invention is a liquid composition comprising an organic diluent and one or more of the above described esterified cellulose ethers of the present invention. The organic diluent may be present in the liquid composition alone or mixed with water. Preferred organic diluents are described further above. The liquid composition preferably comprises at least 5 wt.-%, more preferably at least 10 wt.-%, and preferably up to 30 wt.-%, more preferably up to 20 wt.-% of the esterified cellulose ether of the present invention, based on the total weight of the liquid composition.

The composition of the present invention comprising an aqueous liquid or an organic diluent as described above and one or more of the above described esterified cellulose ethers is also useful as an excipient system for active ingredients and particularly useful as an intermediate for preparing an excipient system for active ingredients, such as fertilizers, herbicides or pesticides, or biologically active ingredients, such as vitamins, herbals and mineral supplements and drugs. Accordingly, the composition of the present invention preferably comprises one or more active ingredients, most preferably one or more drugs. The term "drug" is conventional, denoting a compound having beneficial prophylactic and/or therapeutic properties when administered to an animal, especially humans. In another aspect of the invention the composition of the present invention is used for producing a solid dispersion comprising at least one active ingredient, such as a drug, at least one esterified cellulose ether as described above and optionally one or more adjuvants. A preferred method of producing a solid dispersion is by spray-drying. Spray-drying processes and spray-drying equipment are described generally in Perry's Chemical Engineers' Handbook, pages 20-54 to 20-57 (Sixth Edition 1984). Alternatively, the solid dispersion of the present invention may be prepared by i) blending a) at least one esterified cellulose ether defined above, b) one or more active ingredients and c) one or more optional additives, and ii) subjecting the blend to extrusion. The term "extrusion" as used herein includes processes known as injection molding, melt casting and compression molding. Techniques for extruding, preferably melt-extruding compositions comprising an active ingredient such as a drug are known and described by Joerg Breitenbach, Melt extrusion: from process to drug delivery technology, European Journal of Pharmaceutics and Biopharmaceutics 54 (2002) 107-117 or in European Patent Application EP 0 872 233. The solid dispersion of the present invention preferably comprises a) from 20 to 99.9 percent, more preferably from 30 to 98 percent, and most preferably from 60 to 95 percent of an esterified cellulose ether as described above, and b) preferably from 0.1 to 80 percent, more preferably from 2 to 70 percent, and most preferably from 5 to 40 percent of an active ingredient b), based on the total weight of the esterified cellulose ether a) and the active ingredient b). The combined amount of the esterified cellulose ether a) and the active ingredient b) is preferably at least 70 percent, more preferably at least 80 percent, and most preferably at least 90 percent, based on the total weight of the solid dispersion. The remaining amount, if any, consists of one or more of the adjuvants c) as described below. Once the solid dispersion comprising at least one active ingredient in at least one esterified cellulose ether has been formed, several processing operations can be used, such as drying, granulation, and milling, to facilitate incorporation of the dispersion into a dosage form, such as strands, pellets, granules, pills, tablets, caplets, microparticles, fillings of capsules or injection molded capsules or in the form of a powder, film, paste, cream, suspension or slurry.

The aqueous composition, the liquid composition comprising an organic diluent and the solid dispersion of the present invention may further comprise optional adjuvants, such as coloring agents, pigments, opacifiers, flavor and taste improvers, antioxidants, and any combination thereof.

Some embodiments of the invention will now be described in detail in the following Examples.

EXAMPLES

Unless otherwise mentioned, all parts and percentages are by weight. In the Examples the following test procedures are used.

Content of Ether and Ester Groups

The content of ether groups in the esterified cellulose ether is determined in the same manner as described for "Hypromellose", United States Pharmacopeia and National Formulary, USP 35, pp 3467-3469.

The ester substitution with acetyl groups (—CO—$CH_3$) and the ester substitution with succinoyl groups (—CO—$CH_2$—$CH_2$—COOH) are determined according to Hypromellose Acetate Succinate, United States Pharmacopia and National Formulary, NF 29, pp. 1548-1550". Reported values for ester substitution are corrected for volatiles (determined as described in section "loss on drying" in the above HPMCAS monograph).

Determination of $M_w$ and $M_n$ $M_w$ and $M_n$ are measured according to Journal of Pharmaceutical and Biomedical Analysis 56 (2011) 743 unless stated otherwise. The mobile phase was a mixture of 40 parts by volume of acetonitrile and 60 parts by volume of aqueous buffer containing 50 mM $NaH_2PO_4$ and 0.1 M $NaNO_3$. The mobile phase was adjusted to a pH of 8.0. Solutions of the cellulose ether esters were filtered into a HPLC vial through a syringe filter of 0.45 μm pore size. The exact details of measuring $M_w$ and $M_n$ are disclosed in the International Patent Application No. WO 2014/137777 in the section "Examples" under the title "Determination of $M_w$, $M_n$ and $M_z$".

Water-Solubility

Qualitative Determination at 20° C.:

For the qualitative determination of the water-solubility, a 2 wt. percent solution of HPMCAS in water was prepared by mixing 2.0 g HPMCAS, based on its dry weight, with 98.0 g water under vigorous stirring at 20° C. The dissolution time was 16 hours. The water solubility of the esterified cellulose ether was determined by visual inspection. The determination whether the HPMCAS was water-soluble at 2% or not was done as follows. "Water soluble at 2%—yes" means that a solution without sediment was obtained at 20° C. after 16 hours dissolution time. "Water soluble at 2%—no" means that at least a significant portion of the HPMCAS remained undissolved and formed sediment when mixing 2.0 g HPMCAS, based on its dry weight, with 98.0 g water under vigorous stirring at 20° C.

Quantitative Determination at 2° C.:

2.5 weight parts of HPMCAS, based on its dry weight, were added to 97.5 weight parts of deionized water having a temperature of 2° C. followed by stirring for 6 hours at 2° C. and storing for 16 h at 2° C. A weighed amount of this mixture was transferred to a weighed centrifuge vial; the transferred weight of the mixture was noted as M1 in g. The transferred weight of HPMCAS [M2] was calculated as (transferred weight of mixture in g/100 g*2.5 g). The mixture was centrifuged for 60 min at 5000 rpm (2823×g, Biofuge Stratos centrifuge from Thermo Scientific) at 2° C. After centrifugation an aliquot was removed from the liquid phase and transferred to a dried weighed vial. The weight of the transferred aliquot was recorded as M3 in g. The aliquot was dried at 105° C. for 12 h. The remaining g of HPMCAS was weighted after drying and recorded as M4 in g.

The term "% water soluble at 2.5%" in Table 2 below expresses the percentage of HPMCAS that is actually dissolved in the mixture of 2.5 weight parts of HPMCAS and 97.5 weight parts of deionized water. It is calculated as (M4/M2)*(M1/M3)*100), which corresponds to (g HPMCAS in liquid aliquot/g HPMCAS transferred to centrifuge vial)*(g mixture transferred to centrifuge vial/g liquid aliquot after centrifugation).

Gelation Temperature and Gel Strength of Solutions of HPMCAS in Water

A 2% solution of HPMCAS in water was produced by adding 3 g of milled, ground, and dried HPMCAS (under consideration of the water content of the HPMCAS) to 147 g of water (temperature 20-25° C.) at room temperature while stirring with an overhead lab stirrer at 750 rpm with a 3-wing (wing=2 cm) blade stirrer. The solution was then cooled to about 1.5° C. After the temperature of 1.5° C. was reached the solution was stirred for 120 min at 500 rpms. Each solution was stored in the refrigerator prior to the characterization.

Rheology measurements of 2 wt.-% solutions of the HPMCAS of the present invention in water were conducted with a Haake RS600 (Thermo Fisher Scientific) rheometer with cup and bob fixtures (CC-25). The sample was heated at a rate of 1° C. per minute over a temperature range from 5 to 85° C. with a constant strain (deformation) of 2% and a constant angular frequency of 2 Hz. The measurement collection rate was chosen to be 4 data points/min. The storage modulus G', which was obtained from the rheology measurements, represents the elastic properties of the solution and represents the gel strength in the high temperature region, when the storage modulus G' is higher than the loss modulus G".

The obtained data of the storage modulus G', which was obtained from the oscillation measurements, was first logarithmized and normalized to G' (min) to zero and G' (max) to 100. Linear regression curves were fitted to subsets of these storage modulus data (increments of 5 data points). A tangent was fitted to the steepest slope of the regression curve. The intersection of this tangent with the x-axis is reported as gelation temperature. Details how to determine the gelation temperature are described in International Patent Application WO2015/009796 on pages 18 and 19 in the paragraphs "Determination of the gelation temperature of aqueous compositions comprising methyl cellulose".

The gel strength according to the storage modulus G' at 70° C. was also obtained by this rheology measurement.

Production of HPMCAS of Examples 1-11

Succinic anhydride and acetic anhydride was dissolved at 70° C. in glacial acetic acid. Then hydroxypropyl methyl cellulose (HPMC, water free) and sodium acetate (water free) were added under stirring. The amounts are listed in Table 1 below. The amount of HPMC is calculated on a dried basis. The HPMC had a methoxyl substitution ($DS_M$) and hydroxypropoxyl substitution ($MS_{HP}$) as listed in Table 2 below and a viscosity of 3.0 mPa's, measured as a 2% solution in water at 20° C. according to ASTM D2363-79 (Reapproved 2006). The weight average molecular weight of the HPMC was about 20,000 Dalton. The HPMC is commercially available from The Dow Chemical Company as Methocel E3 LV Premium cellulose ether.

Then the reaction mixture was heated up to the reaction temperature listed in Table 1 below. The reaction time during which the mixture was allowed to react is also listed in Table 1 below. Then the crude product was precipitated by adding 1.8-2.4 L of water having a temperature of 50 to 100° C. Subsequently the precipitated product was separated from the mixture by filtration. The separated product was washed several times by re-suspension under high-shear with hot water (95° C.), each time followed by filtration. Then the product was dried at 55° C. overnight.

Production of HPMCAS of Comparative Examples CE-11 to CE-16, CE-D and CE-E, as Described in WO 2014/137777

Comparative Examples CE-11 to CE-16 and Comparative Examples CE-D and CE-E correspond to Examples 11-16 and Comparative Examples D and E of the International Patent Application No. WO 2014/137777. Their production is described in detail in the International Patent Application WO 2014/137777 on pages 22 and 23.

Production of HPMCAS of Comparative Example CE-C, as Described in WO/2014/031422

Comparative Example CE-C corresponds to Comparative Example C of the International Patent Application WO/2014/031422. Its production is described in detail in the International Patent Application WO/2014/031422 on page 25.

Comparative Examples CE-H to CE-J

Comparative Examples CE-H to CE-J correspond to Comparative Examples H to J of the International Patent Application No. WO 2014/137777.

As disclosed in International Patent Application WO 2011/159626 on pages 1 and 2 and in International Patent Application WO 2005/115330 on pages 6 and 7, HPMCAS is currently commercially available from Shin-Etsu Chemical Co., Ltd. (Tokyo, Japan), known by the trade name "AQOAT". Shin-Etsu manufactures three grades of AQOAT polymers that have different combinations of substituent levels to provide enteric protection at various pH levels, AS-L, AS-M, and AS-H, typically followed by the designation "F" for fine or "G", such as AS-LF or AS-LG. Their sales specifications are listed below. According to the Technical Brochure of Shin-Etsu "Shin-Etsu AQOAT Enteric Coating Agent" edition 04.9 05.2/500, all grades of AQOAT polymers are soluble in 10% NaOH but insoluble in purified water. Samples of the commercially available materials were analyzed as described further above.

| | Designation of analyzed commercial samples: Comparative Example | | |
|---|---|---|---|
| | CE-H | CE-I | CE-J |
| | Published Composition of AQOAT polymers (wt %) | | |
| Substituent content | L-Grade | M-Grade | H-Grade |
| Methoxyl | 20.0-24.0 | 21-0-25.0 | 22.0-26.0 |
| Hydroxypropoxyl | 5.0-9.0 | 5.0-9.0 | 6.0-10.0 |
| Acetyl | 5.0-9.0 | 7.0-11.0 | 10.0-14.0 |
| Succinoyl | 14.0-18.0 | 10-14 | 4.0-8.0 |

| | | L Grades | | M Grades | | H Grades | |
|---|---|---|---|---|---|---|---|
| Item | Substituent | Range* | Average (of 12 lots) | Range* | Average (of 28 lots) | Range* | Average (of 17 lots) |
| Manufacturer's Certificate of Analysis (wt %) | Methoxyl | 21.7-22.5 | 22.1 ± 0.3 | 22.7-23.6 | 23.1 ± 0.2 | 23.2-24.1 | 23.7 ± 0.3 |
| | Hydroxypropoxyl | 6.8-7.1 | 7.0 ± 0.1 | 7.0-7.9 | 7.3 ± 0.2 | 7.1-7.8 | 7.5 ± 0.2 |
| | Acetyl | 7.2-8.1 | 7.7 ± 0.3 | 8.7-10.8 | 9.3 ± 0.4 | 11.0-12.2 | 11.5 ± 0.3 |
| | Succinoyl | 15.1-16.5 | 15.5 ± 0.4 | 10.8-11.5 | 11.2 ± 0.2 | 5.3-7.6 | 6.5 ± 0.7 |
| Calculated Degree of Substitution | DOSM | 1.84-1.91 | 1.87 ± 0.03 | 1.85-1.94 | 1.89 ± 0.02 | 1.84-1.92 | 1.88 ± 0.02 |
| | DOSHP | 0.24-0.25 | 0.25 ± 0.01 | 0.24-0.27 | 0.25 ± 0.01 | 0.23-0.26 | 0.24 ± 0.01 |
| | DOSAc | 0.44-0.49 | 0.47 ± 0.02 | 0.51-0.65 | 0.55 ± 0.03 | 0.62-0.70 | 0.66 ± 0.02 |
| | DOSs | 0.39-0.43 | 0.40 ± 0.01 | 0.27-0.29 | 0.28 ± 0.01 | 0.13-0.19 | 0.16 ± 0.02 |

-continued

| Item | Substituent | L Grades Range* | Average (of 12 lots) | M Grades Range* | Average (of 28 lots) | H Grades Range* | Average (of 17 lots) |
|---|---|---|---|---|---|---|---|
| | DOSM + DOSAc + DOSs | 2.70-2.80 | 2.75 ± 0.03 | 2.65-2.87 | 2.71 ± 0.03 | 2.63-2.73 | 2.70 ± 0.03 |
| | DOSAc + DOSs | 0.85-0.89 | 0.88 ± 0.01 | 0.80-0.93 | 0.83 ± 0.03 | 0.77-0.84 | 0.81 ± 0.02 |

*Range of several lots of polymer for each grade (the number of lots is indicated under "Average").
**Degree of substitution calculated as described in WO 2011/159626

The properties of the HPMCAS of Examples 1-11, Comparative Examples CE-11 to CE-16 and Comparative Examples CE-C, CE-D, CE-E and CE-H to CE-J are listed in Table 2 below. In Table 2 the abbreviations have the following meanings:
$DS_M$=DS(methoxyl): degree of substitution with methoxyl groups;
$MS_{HP}$=MS(hydroxypropoxyl): molar subst. with hydroxypropoxyl groups;
$DS_{Ac}$: degree of substitution of acetyl groups;
$DS_S$: degree of substitution of succinoyl groups.

TABLE 1

| (Comp.) Example | HPMC* g | HPMC* Mol | HPMC, 2% viscosity in water (mPa·s) | Glacial acetic acid g | Glacial acetic acid HPMC | Succinic anhydride g mol/mol | Succinic anhydride HPMC | Acetic anhydride g mol/mol | Acetic anhydride HPMC | Sodium acetate g mol/mol | Sodium acetate HPMC | Reaction temperature (°C.) | Reaction time (hours) |
|---|---|---|---|---|---|---|---|---|---|---|---|---|---|
| 1 | 230 | 1.14 | 3.0 | 500 | 7.3 | 8.0 | 0.07 | 25.0 | 0.22 | 230 | 2.46 | 85 | 3.5 |
| 2 | 230 | 1.14 | 3.0 | 500 | 7.3 | 6.0 | 0.05 | 25.0 | 0.22 | 230 | 2.46 | 85 | 3.0 |
| 3 | 230 | 1.14 | 3.0 | 500 | 7.3 | 4.0 | 0.04 | 25.0 | 0.22 | 230 | 2.46 | 85 | 3.5 |
| 4 | 230 | 1.14 | 3.0 | 500 | 7.3 | 2.0 | 0.02 | 25.0 | 0.22 | 230 | 2.46 | 85 | 3.5 |
| 5 | 230 | 1.14 | 3.0 | 500 | 7.3 | 10.0 | 0.09 | 30.6 | 0.27 | 230 | 2.46 | 85 | 3.5 |
| 6 | 230 | 1.14 | 3.0 | 600 | 8.8 | 30.0 | 0.26 | 10.2 | 0.09 | 230 | 2.46 | 85 | 3.5 |
| 7 | 230 | 1.14 | 3.0 | 600 | 8.8 | 20.0 | 0.18 | 15.0 | 0.13 | 230 | 2.46 | 85 | 3.5 |
| 8 | 230 | 1.14 | 3.0 | 500 | 7.3 | 16.0 | 0.14 | 17.0 | 0.15 | 230 | 2.46 | 85 | 3.5 |
| 9 | 230 | 1.14 | 3.0 | 500 | 7.3 | 17.0 | 0.15 | 24.0 | 0.22 | 230 | 2.46 | 85 | 3.5 |
| 10 | 230 | 1.14 | 3.0 | 500 | 7.3 | 10.0 | 0.09 | 26.0 | 0.23 | 230 | 2.47 | 85 | 3.5 |
| 11 | 230 | 1.14 | 3.0 | 500 | 7.3 | 12.0 | 0.11 | 30.0 | 0.27 | 230 | 2.47 | 85 | 3.5 |
| CE-11 | 215 | 1.06 | 1.5 | 231 | 3.6 | 35.5 | 0.33 | 130.2 | 1.25 | 86.9 | 1.00 | 85 | 3.5 |
| CE-12 | 60 | 0.3 | 1.39 | 35 | 2.0 | 10.1 | 0.34 | 37.2 | 1.28 | 17.4 | 0.72 | 85 | 3.5 |
| CE-13 | 60 | 0.3 | 1.39 | 30 | 1.7 | 10.1 | 0.34 | 37.2 | 1.28 | 17.4 | 0.72 | 85 | 3.5 |
| CE-14 | 100 | 0.49 | 2.0 | 135 | 4.5 | 16.9 | 0.34 | 62 | 1.28 | 41.4 | 1.02 | 85 | 3.5 |
| CE-15 | 100 | 0.49 | 2.0 | 126 | 4.3 | 16.9 | 0.34 | 62 | 1.28 | 41.4 | 1.02 | 85 | 3.5 |
| CE-16 | 100 | 0.49 | 2.0 | 117 | 4 | 16.9 | 0.34 | 62 | 1.28 | 41.4 | 1.02 | 85 | 3.5 |
| CE-C | 150 | 0.74 | 3.0 | 450 | 10.1 | 35.8 | 0.48 | 57.43 | 0.79 | 59.57 | 0.98 | 85 | 3.5 |
| CE-D | 195.0 | 0.97 | 3.1 | 442 | 7.6 | 54.6 | 0.57 | 253.5 | 2.69 | 195 | 2.47 | 85 | 3.5 |
| CE-E | 200 | 0.96 | 3.1 | 600 | 10.2 | 50.0 | 0.51 | 76 | 0.78 | 160 | 1.97 | 3.5 | 2.4 |

*Calculated on a dried basis

TABLE 2

| (Comparative) Ex. | Molecular weight (kDA) $M_n$ | Molecular weight (kDA) $M_w$ | Methoxyl (%) | Hydroxypropoxyl (%) | Acetyl (%) | Succinoyl (%) | $DS_M$ | $MS_{HP}$ | $DS_{Ac}$ | $DS_S$ | Sum $DS_{Ac}$ + $DS_S$ | % water soluble at 2.5% | Water-soluble at 2% |
|---|---|---|---|---|---|---|---|---|---|---|---|---|---|
| 1 | 21 | 28 | 28.8 | 8.6 | 1.9 | 2.6 | 1.99 | 0.25 | 0.09 | 0.03 | 0.12 | n.m. | yes |
| 2 | 20 | 27 | 29.0 | 8.6 | 1.8 | 1.9 | 1.99 | 0.24 | 0.10 | 0.01 | 0.11 | n.m. | yes |
| 3 | 19 | 25 | 29.2 | 8.9 | 1.9 | 1.3 | 1.84 | 0.18 | 0.19 | 0.08 | 0.27 | 100 | yes |
| 4 | 19 | 25 | 29.5 | 8.6 | 2.1 | 0.7 | 1.86 | 0.18 | 0.04 | 0.14 | 0.18 | n.m. | yes |
| 5 | 28 | 41 | 26.6 | 6.3 | 3.9 | 3.7 | 1.87 | 0.18 | 0.05 | 0.08 | 0.13 | n.m. | yes |
| 6 | 33 | 41 | 26.9 | 6.3 | 0.8 | 6.7 | 1.99 | 0.25 | 0.06 | 0.10 | 0.15 | n.m. | yes |
| 7 | 31 | 39 | 27.7 | 6.5 | 1.1 | 3.9 | 1.97 | 0.25 | 0.08 | 0.11 | 0.20 | 101 | yes |

TABLE 2-continued

| (Comparative) Ex. | Molecular weight (kDA) $M_n$ | Molecular weight (kDA) $M_w$ | Methoxyl (%) | Hydroxy-propoxyl (%) | Acetyl (%) | Succinoyl (%) | $DS_M$ | $MS_{HP}$ | $DS_{Ac}$ | $DS_S$ | Sum $DS_{Ac} + DS_S$ | % water soluble at 2.5% | Water-soluble at 2% |
|---|---|---|---|---|---|---|---|---|---|---|---|---|---|
| 8 | 23 | 28 | 28.5 | 8.8 | 1.1 | 4.5 | 1.97 | 0.25 | 0.10 | 0.07 | 0.17 | n.m. | yes |
| 9 | 22 | 29 | 27.9 | 8.6 | 1.6 | 5.3 | 1.97 | 0.25 | 0.11 | 0.09 | 0.20 | n.m. | yes |
| 10 | 21 | 27 | 28.3 | 8.8 | 2.0 | 3.3 | 1.99 | 0.25 | 0.09 | 0.03 | 0.12 | n.m. | yes |
| 11 | 21 | 27 | 28.1 | 8.7 | 2.2 | 4.0 | 1.99 | 0.24 | 0.10 | 0.01 | 0.11 | n.m. | yes |
| CE-11 | 11 | 24 | 23.1 | 7.8 | 10.0 | 11.3 | 1.93 | 0.27 | 0.60 | 0.29 | 0.89 | 71 | no |
| CE-12 | 10 | 41 | 22.7 | 7.7 | 9.8 | 12.3 | 1.91 | 0.27 | 0.59 | 0.32 | 0.91 | 50 | no |
| CE-13 | 12 | 112 | 22.7 | 7.7 | 10.2 | 11.6 | 1.90 | 0.27 | 0.62 | 0.30 | 0.92 | 51 | no |
| CE-14 | 16 | 68 | 23.4 | 7.8 | 9.1 | 11.5 | 1.94 | 0.27 | 0.54 | 0.29 | 0.83 | 62 | no |
| CE-15 | 20 | 105 | 23.3 | 7.8 | 9.4 | 11.7 | 1.94 | 0.27 | 0.56 | 0.30 | 0.86 | 51 | no |
| CE-16 | 28 | 158 | 23.1 | 7.9 | 9.3 | 11.4 | 1.91 | 0.27 | 0.56 | 0.29 | 0.85 | 43 | no |
| CE-C | 23 | 53 | 23.7 | 7.6 | 5.8 | 14.7 | 1.96 | 0.26 | 0.35 | 0.37 | 0.72 | 67 | no |
| CE-D | 36 | 139 | 22.7 | 7.5 | 11.0 | 12.1 | 1.94 | 0.26 | 0.68 | 0.32 | 1.00 | 11 | no |
| CE-E | 26 | 65 | 22.9 | 7.3 | 5.7 | 16.0 | 1.91 | 0.25 | 0.34 | 0.41 | 0.75 | 51 | no |
| CE-H | 33 | 153 | 22.5 | 7.0 | 8.1 | 14.7 | 1.90 | 0.24 | 0.49 | 0.38 | 0.87 | 12 | no |
| CE-I | 27 | 114 | 23.1 | 7.3 | 9.3 | 10.6 | 1.88 | 0.24 | 0.54 | 0.26 | 0.76 | 45 | no |
| CE-J | 29 | 137 | 23.6 | 7.2 | 11.6 | 7.9 | 1.90 | 0.24 | 0.67 | 0.19 | 0.86 | 31 | no | n.m.: not measured

The esterified cellulose ethers of Examples 1-11 were soluble at a concentration of 2 wt.-% in water at a temperature of 21° C.

In contrast thereto, the esterified cellulose ethers of Comparative Examples A-E and CE-D, DE-E and CE-H-CE-J could not brought into solution at a concentration of 2 wt.-% in water at a temperature of 21° C. In each Comparative Example at least a portion of the 2 wt.-% HPMCAS remained undissolved and formed sediment in water at 21° C.

Gelation

Figure 2:
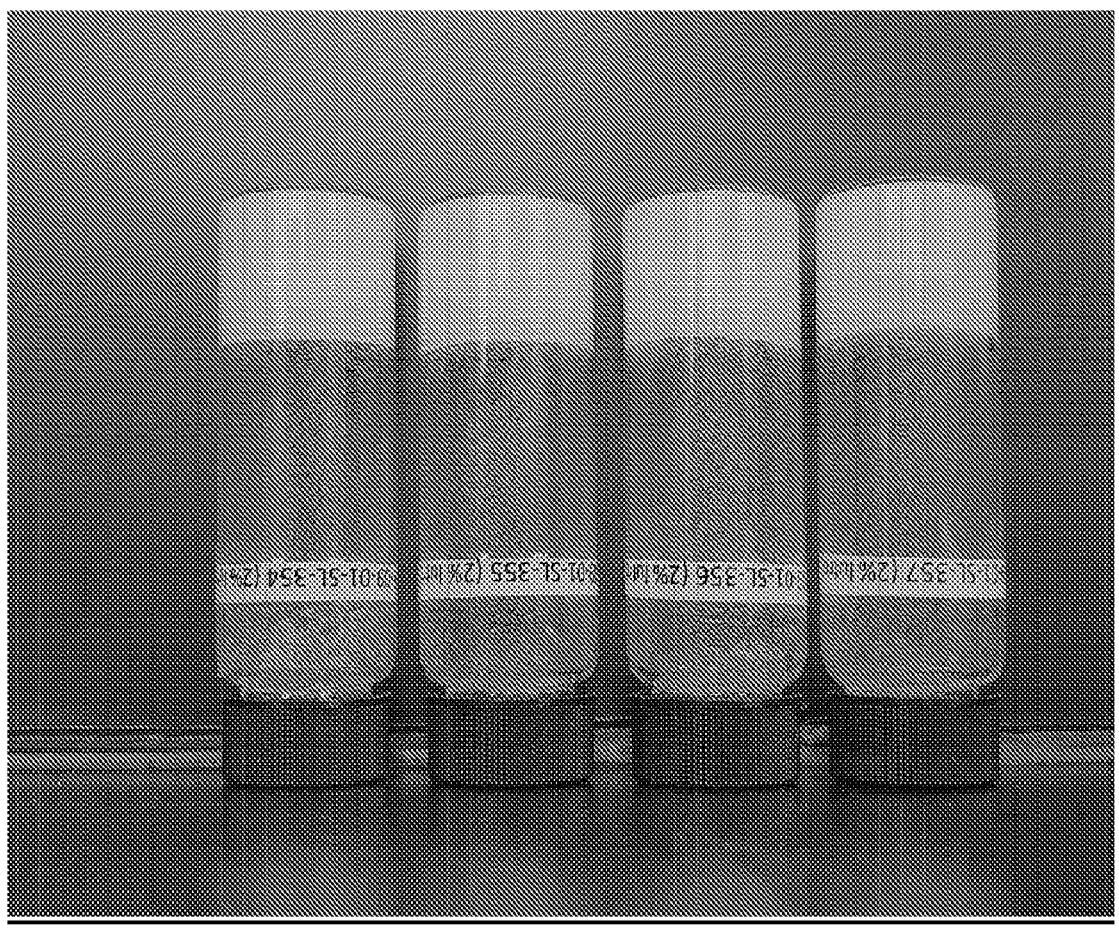
FIG. 2 is a photographical representation of 2 wt.-% solutions of HPMCAS of Examples 1-4 in water after heating the solutions to 70° C. The glass bottles containing the HPMCAS solution have been turned upside down to illustrate that the HPMCAS solutions have formed a gel.

Aqueous solutions of the esterified hydroxyalkyl alkyl celluloses of the present invention, particularly HPMCAS, gel at elevated temperature, typically at 45 to 90° C., more typically at 50 to 80° C., even at a concentration as low as 2 wt. %. It is very surprising that the esterified hydroxyalkyl alkyl celluloses gel in spite of their very low total degree of ester substitution. Glass bottles containing 2 wt.-% solutions of a HPMCAS of Examples 1-4 in water can be turned upside down after heating the solutions to 70° C. without causing the gelled HPMCAS to flow. FIG. 2 is a photographical representation of 2 wt.-% solutions of HPMCAS of Examples 1-4 in water after heating the solutions to 70° C. The glass bottles containing the HPMCAS solution have been turned upside down to illustrate that the HPMCAS solutions have formed a gel.

Figure 1B:
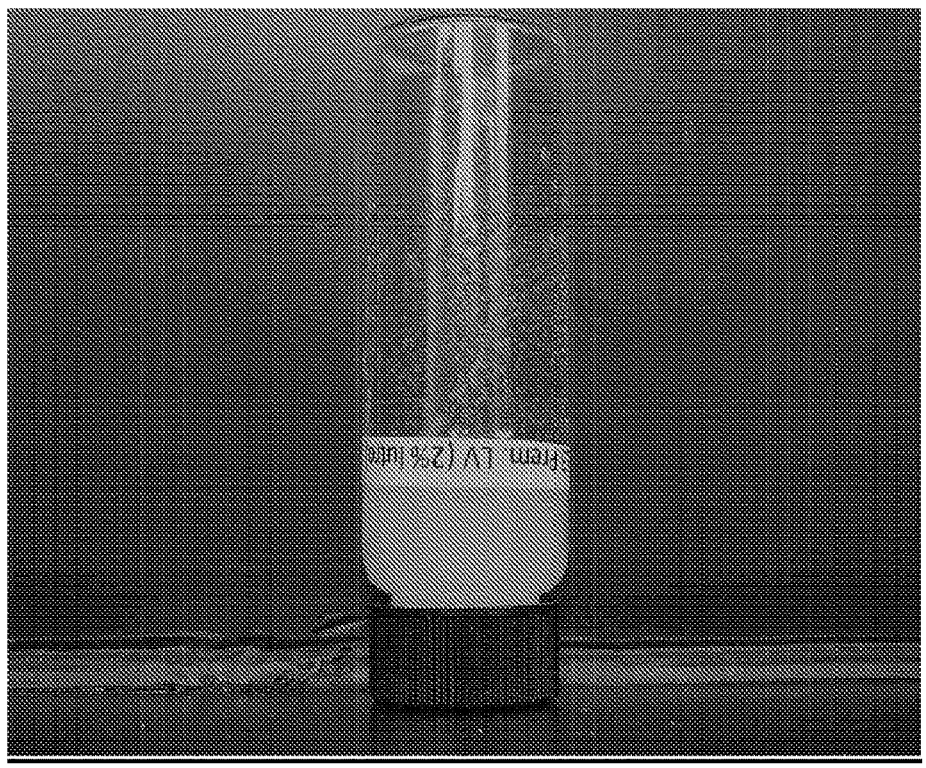
FIG. 1B is a photographical representation of the 2 wt.-% HPMC solution in water represented in FIG. 1A, except that the glass bottle containing the HPMC solution has been turned upside down.

The HPMC that was used as starting material for preparing the HPMCAS of Examples 1-11 does not gel. A 2 wt.-% solution of Methocel E3 LV Premium cellulose ether in water after heating to 70° C. does not form a gel but only flocculates. When the glass bottle is turned upside down, the HPMC solution flows from the bottom of the bottle to its lid. FIG. 1A is a photographical representation of a 2 wt.-% solution of Methocel E3 LV Premium cellulose ether in water after heating to 70° C. FIG. 1B is a photographical representation of the 2 wt.-% HPMC solution in water represented in FIG. 1A, except that the glass bottle containing the HPMC solution has been turned upside down. FIG. 1B illustrates that the HPMC does not form a gel but only flocculates. When the glass bottle is turned upside down, the HPMC solution flows from the bottom of the bottle to its lid.

Rheology measurements were carried out to measure the gelation temperatures and gel strength according to the storage modulus G' at 70° C. of 2 wt.-% solutions of the HPMCAS of Examples 1 to 11 in water as described further above. The results are listed in Table 3 below.

TABLE 3

| Example | Gelation Temperature, ° C. | Gel Strength G' at 70° C., Pa |
|---|---|---|
| 1 | 52 | 125 |
| 2 | 53 | 112 |
| 3 | 49 | 78 |
| 4 | 54 | 81 |
| 5 | 50 | 154 |
| 6 | 54 | 80 |
| 7 | 61 | 35 |
| 8 | 52 | 65 |
| 9 | 50 | 140 |
| 10 | 52 | 112 |
| 11 | 50 | 140 |
| Methocel E3 LV Premium cellulose ether | 55 | 1.8* |
| HPMCAS neutralized with NH$_4$HCO$_3$ | No gelling | <1 |

*No significant gelling, only flocculation

For comparative purposes a commercially available HPMCAS was neutralized with NH$_4$HCO$_3$ to adjust its pH to 6.3. The HPMCAS had 23.5% methoxyl groups ($DS_{methoxyl}$=1.93), 7.3% hydroxypropoxyl groups ($MS_{hydroxypropoxyl}$=0.25), 9.8% acetyl groups ($DS_{acetyl}$=0.58), 10.5% succinoyl groups ($DS_{succinoyl}$=0.26), and a viscosity of 2.9 mPa·s, measured as a 2.0% by weight solution of the HPMCAS in 0.43 wt. % aqueous NaOH.

2 and 5 wt.-% solutions of the HPMCAS in water were prepared. When preparing 100 g of a 2 wt.-% solution of HPMCAS in water, 0.19 g of NH$_4$HCO$_3$ was used for neutralization; the resulting degree neutralization of the HPMCAS was 96%. When preparing 100 g of a 5 wt.-% solution of HPMCAS in water, 0.43 g of NH$_4$HCO$_3$ was used for neutralization; the resulting degree neutralization of the HPMCAS was 87%. Rheology measurements were carried out. No gelling occurred.

The invention claimed is:

1. An esterified cellulose ether comprising aliphatic monovalent acyl groups and groups of the formula —C(O)—R—COOH, R being a divalent hydrocarbon group, wherein
  i) the degree of neutralization of the groups —C(O)—R—COOH is not more than 0.4, ii) the total degree of ester substitution is from 0.03 to 0.38, and iii) the esterified cellulose ether has a solubility in water of at least 2.0 weight percent at 20° C., wherein the esterified cellulose ether is hydroxypropyl methylcellulose acetate succinate (HPMCAS).

2. The esterified cellulose ether of claim 1 wherein the total degree of ester substitution is from 0.09 to 0.27.

3. The esterified cellulose ether of claim 1 having a degree of substitution of aliphatic monovalent acyl groups of from 0.03 to 0.20 and a degree of substitution of groups of formula —C(O)—R—COOH of from 0.01 to 0.15.

4. The esterified cellulose ether of claim 1 having a weight average molecular weight $M_w$ of up to 100,000 Dalton.

5. The esterified cellulose ether of claim 1 wherein at least 85 wt. % of the esterified cellulose ether is soluble in a mixture of 2.5 weight parts of the esterified cellulose ether and 97.5 weight parts of water at 2° C.

6. An aqueous composition comprising an esterified cellulose ether of claim 1 dissolved in an aqueous liquid.

7. The aqueous composition of claim 6 comprising at least 10 weight percent of the esterified cellulose ether, based on the total weight of the aqueous composition.

8. A liquid composition comprising at least one esterified cellulose ether of claim 1 and an organic diluent.

9. A process for coating a dosage form comprising the step of contacting an aqueous composition comprising an esterified cellulose ether of claim 1 dissolved in an aqueous liquid with the dosage form.

10. A process for the manufacture of capsule shells comprising the step of contacting an aqueous composition comprising an esterified cellulose ether of claim 1 dissolved in an aqueous liquid with dipping pins.

11. A coated dosage form wherein the coating comprises at least one esterified cellulose ether of claim 1.

12. A polymeric capsule shell comprising at least one esterified cellulose ether of claim 1.

13. A capsule comprising a capsule shell of claim 12 and further comprising a drug or a nutritional or food supplement or a combination thereof.

14. A solid dispersion of at least one active ingredient in at least one esterified cellulose ether of claim 1.

15. The aqueous composition of claim 6 wherein the esterified cellulose ether of claim 1 is dissolved in the aqueous liquid to form an aqueous solution, and the aqueous solution gels at an elevated temperature of from 50° C. to 90° C.

16. The esterified cellulose ether of claim 1 having a viscosity of at least 2.4 mPa·s, measured as a 2.0 wt. % solution of the esterified cellulose ether in 0.43 wt. % aqueous NaOH at 20° C.

17. The esterified cellulose ether of claim 1 having a viscosity of at least 2.8 mPa·s, measured as a 2.0 wt. % solution of the esterified cellulose ether in 0.43 wt. % aqueous NaOH at 20° C.

* * * * *